United States Patent
Vellinga (10) Patent No.: US 9,534,194 B2
(45) Date of Patent: Jan. 3, 2017

(54) REACTOR FOR BULK PRODUCTION OF PHOTOSYNTHETIC MICROORGANISMS

(71) Applicant: Micro Resources Ltd., Wanchai (HK)

(72) Inventor: Sjoerd Hubertus Jozef Vellinga, Tjalleberd (NL)

(73) Assignee: Micro Resources LTD., Wanchai (HK)

( * ) Notice: Subject to any disclaimer, the term of this patent is extended or adjusted under 35 U.S.C. 154(b) by 0 days.

(21) Appl. No.: 14/778,523

(22) PCT Filed: Mar. 21, 2014

(86) PCT No.: PCT/NL2014/050172
§ 371 (c)(1),
(2) Date: Sep. 18, 2015

(87) PCT Pub. No.: WO2014/148903
PCT Pub. Date: Sep. 25, 2014

(65) Prior Publication Data
US 2016/0186109 A1    Jun. 30, 2016

(30) Foreign Application Priority Data

Mar. 21, 2013 (EP) ..................................... 13160450

(51) Int. Cl.
*C12M 1/00* (2006.01)
*C12M 3/00* (2006.01)
(Continued)

(52) U.S. Cl.
CPC ............. *C12M 21/02* (2013.01); *C12M 29/08* (2013.01); *C12M 31/08* (2013.01); *C12M 39/00* (2013.01); *C12P 7/64* (2013.01); *G06Q 30/04* (2013.01)

(58) Field of Classification Search
CPC ....... C12M 21/02; C12M 29/08; C12M 31/08; C12M 39/00; C12P 7/64
(Continued)

(56) References Cited

U.S. PATENT DOCUMENTS 5,104,803 A * 4/1992 Delente .................. C12M 21/02
362/101
5,151,347 A * 9/1992 Delente .................. C12M 21/02
435/168

(Continued)

FOREIGN PATENT DOCUMENTS

JP      H08 262231 A    10/1996
JP      H08 262232 A    10/1996
(Continued)

OTHER PUBLICATIONS

International Search Report issued in International Patent Application No. PCT/NL2014/050172 mailed Feb. 7, 2014.

*Primary Examiner* — Michael Hobbs
(74) *Attorney, Agent, or Firm* — Foley & Lardner LLP; Sunit Talapatra (57) ABSTRACT

An algae production reactor system comprising a reactor vessel which is disclosed. The system comprises (a) one or more liquid inlets and one or more liquid outlets; (b) one or more gas inlets at the bottom, the gas inlets being connected with a source of carbon dioxide, and one or more gas outlets at the top of the vessel; and (c) vertically interspaced and joined pairs of double glass plates which are at least partially submerged in the reactor liquid, the double glass plates having a layer of light-scattering particles in between and having a flat side being exposed to a light source, wherein part of the spaces between the double glass plates is arranged above the gas inlets for vertically circulating reactor liquid.

17 Claims, 5 Drawing Sheets

(51) Int. Cl.
*G06Q 30/04* (2012.01)
*C12P 7/64* (2006.01)

(58) Field of Classification Search
USPC .......................................... 435/292.1; 47/1.4
See application file for complete search history.

(56) References Cited

U.S. PATENT DOCUMENTS

| | | | | |
|---|---|---|---|---|
| 5,162,051 | A * | 11/1992 | Hoeksema | C12M 21/02 362/101 |
| 6,083,740 | A * | 7/2000 | Kodo | B01D 53/84 435/257.1 |
| 6,287,852 | B1 * | 9/2001 | Kondo | C12M 21/02 435/292.1 |
| 2009/0047722 | A1 * | 2/2009 | Wilkerson | C12M 21/02 435/173.7 |
| 2010/0028991 | A1 * | 2/2010 | McCall | F24J 2/1047 435/292.1 |

FOREIGN PATENT DOCUMENTS

| | | |
|---|---|---|
| JP | H10 108665 A | 4/1998 |
| JP | 2000 300244 A | 10/2000 |
| WO | WO 2008/015865 A2 | 5/2008 |
| WO | WO 2010/025345 A2 | 3/2010 |

* cited by examiner

REACTOR FOR BULK PRODUCTION OF PHOTOSYNTHETIC MICROORGANISMS

CROSS-REFERENCE TO RELATED APPLICATIONS

This application is the National Phase of International Patent Application No. PCT/NL2014/050172, filed Mar. 21, 2014, published on Sep. 25, 2014 as WO 2014/148903 A1, which claims priority to European Application No. 13160450.6, filed Mar. 21, 2013. The contents of which are herein incorporated by reference in its entirety.

FIELD OF THE INVENTION

The present invention relates to the production of algae and is particularly concerned with the growth of algae in an enclosed reactor system where the sunlight can be fed into the reactor by a mirror system. The invention provides a reactor vessel and light-introducing means for such an algal production reactor system.

BACKGROUND

Algae use light and carbon dioxide for growing and this process generates oxygen. Normally algae are produced in open ponds, transparent piping systems, submerged plastic bags, etc.

The disadvantages of these systems are the amount of energy necessary for mixing, feeding the carbon source and removal of the generated oxygen. Also the amount of water evaporation, heating of the water in daytime and the cooling in the night is a problem. This is because the only sensible source of light for growing algae is sunlight, which is in principle available for free, but for optimum growth, the algae require a high influx of light. However, sites where high sunlight input is available are almost inherently hampered by being located in arid zones of the earth, where water, also necessary for algal production, is very scarce.

These disadvantages limit the algae concentration in the reactor systems and increase thus the amount of reactor space necessary for a specific amount of algae production. Thus there is need for more efficacious and up-scalable reactor vessels for growing photosynthetic microorganisms with improved light supply.

JP-A 2000-300244 discloses a photosynthetic culturing device having light-transmitting plates made of acrylic, which are arranged vertically in a reactor, the (sun)light entering on the top of the reactor. The distance of 10-70 mm between the plates provides the reactor space containing the culture medium in an up-flow arrangement. The top ends of the spaces between the plates are closed with covers ("first invention") or with triangular extensions of the acrylic plates for increased irradiation surface ("second invention"). The light-transmitting plates may have light-scattering surfaces provided by unidirectional striping, and pairs of plates may be formed in such a way that the light-scattering surfaces are at the inner side of the pairs, as described in JP-A H08-262232.

The reactors of the types descried in JP-A 2000-300244 and JP-A H08-262232 do not provide for optimum irradiation efficiency and algal production rates. Moreover, the arrangement nature of the plates used according to this prior art do not allow the provision of robust, large scale photosynthesis reactors for use at remote sites and requiring minimum maintenance operations.

SUMMARY OF THE INVENTION

It was found according to the invention, that improved photosynthesis can be provided by means of a reactor of an airlift-loop type, using lateral irradiation, and by providing unit pairs of double rectangular glass plates which are mounted in parallel at a distance provided by glass strips arranged between the rectangular double glass plates and along the long (vertical) sides of the double glass plates. The use of glass plates rather than acrylic-type plates reduces fouling by microorganisms. Further improvement is achieved by providing light-scattering layers at the inside of the double glass plates, the light scattering layers comprising non-unidirectional layers of non-uniformities or particles.

The invention thus provides a large-scale reactor for growing algae which has an upward flow and a downward flow channel, which can alternate e.g. by switching the feeds of the gas mixing flow. Gas can induce the upward and downward flow circulation. These types of airlift loop reactors are known as such in waste water treatment. Vertical glass plates are arranged in the upward and in the downward flow. The front parts of these glass plates are sticking out of the reactor wall into a (sun)light source, together with glass strips joining pairs of double glass plates along their long (vertical) sides. These glass plates are used to transfer light into the reactor which is necessary for algal growth inside the reactor.

DESCRIPTION OF THE INVENTION

The invention therefore pertains to a reactor vessel for the production of photosynthetic microorganisms. Such a reactor is also referred to by its synonyms "photosynthesis reactor" or "photobioreactor". The reactor vessel is provided with one or more liquid inlets and one or more liquid outlets, one or more gas inlets at the bottom and one or more gas outlets at the top of the vessel, and vertically interspaced sets of double glass plates which are at least partially submerged in the reactor liquid when the reactor vessel is in operation. The double glass plates have a layer of light-scattering particles in between and have a flat side corresponding to the thickness of the double glass plates, which flat side is being exposed to an external light source. In operation, the flat sides are suitably vertically. The reactor vessel is further provided with means for vertically circulating reactor liquid. The reactor as ready for operation also contains the further means and materials for producing algae by photosynthesis, including a suitable inoculate of the algae to be produced, a source of carbon dioxide, etc.

The double glass plates, which are arranged pair-wise, constitute an important element of the reactor vessel of the invention and of the invention itself. The refractive index of the glass is higher than the refractive index of water, which makes the glass plates function like a glass fibre used for data transport. The layer of light-scattering particles ensures that the light leaks out evenly over the submerged area of the glass plate into the reactor liquid. For this purpose the glass plates consist of two layers (referred to as "double glass plates") with a coating in between which constitutes a matrix for small (i) inorganic (e.g. metal oxide) or (ii) organic particles or (iii) non-uniformities to scatter the light, or for (iv) larger mirror facets to reflect the light in such a way that the light can enter the water face.

The (single) glass plates can have a thickness varying from a few mm, e.g. 5 mm, up to about 50 mm or even more. Advantageously, the thickness of the glass plates is between 10 and 30 mm, most preferably between 12 and 20 mm.

Thus, the double glass plates preferably have a thickness between 20 and 60 mm, most preferably between 24 and 40 mm. Similarly, the flat sides of the double glass plates also preferably have a breadth of 20-60, or 24-40 mm. The glass is preferably of the so-called "ultra-clear" type, i.e. it has a high clarity and is low in iron, in particular below 0.04 wt. % (as $Fe_2O_3$). Such glasses are also called low-iron glass, or high transmittance glass.

The layer of light-scattering particles can be a coating layer in which the scattering particles are mixed in a material having the same or nearly the same refractive index as glass, so that light can pass from glass to coating without a mirror effect caused by a difference in refractive index. For instance it can be a ceramic coating such as silica. In the coating layer non-uniformities can be mixed which cause the scattering (for instance crystallites, bubbles etc.). Non-uniformities are understood to be bodies or voids which constitute a discontinuity in the matrix, i.e. which can be, at least electromagnetically, distinguished from the surrounding coating, for example by their refractive index. The non-uniformities are preferably substantially spherical.

Two types of scattering can be used: (1) Mie-scattering, with non-uniformities or particles with about the same or slightly larger (average) size than the wavelength of visible light, preferably in the range of 200-1200 nm, more preferably in the range from 300 up to 1000 nm, most preferably at least 400 nm, up to e.g. 800 nm; (2) Geometric scattering, with particles much larger than the wavelength of light, preferably in the range from 5 micrometer up to 500 micrometer, for instance chromium crystals.

The Mie scatterers (non-uniformities) may be metal oxides e.g. of titanium, zinc, silicon, or aluminium, or silicates, e.g. of magnesium or aluminium. Alternatively, the Mie scatterers may be organic particles, e.g. polymer (latex) particles, or they may be (pores, bubbles) of the same size. Particles of metal oxides, in particular titanium dioxide, are particularly preferred, e.g. of 0.3 to 1 μm.

The geometric scatterers are facetted (mirroring) particles, i.e. particles having light-reflecting facets, such as in chromium crystals or mono crystalline micro diamonds (6-20 μm). They preferably have sizes in the range of 5-500 μm, more preferably 10-200 μm, in particular 20-200 μm.

The thickness of the internal coating containing the light-scattering non-uniformities or particles depends on the type of scattering. For Mie-scattering it is preferably in the range of 5 to 500 μm, especially between 10 and 200 μm, and for the geometric scattering it is preferably between 100 and 1000 μm. The particles are advantageously homogeneously distributed in the internal coating. Their density may be e.g. between 1 and 500 mg per $dm^2$ of the coating (matrix).

The distance between pairs of double glass plates, i.e. the effective reactor space, may be as close as e.g. 10 mm, up to, say 20 cm or more. For an optimum light irradiation, it is preferred that the distance is between about the thickness of the double plates and about twice said thickness, i.e. between 20 and 120 mm, most preferably between 24 and 80 mm. The number of double glass plates over the width of the reactor may vary. Preferably the reactor vessel, or reactor unit, contains between 4 and 25, more preferably between 6 and 20 double glass plates per m of reactor width, the glass plates being essentially mounted in parallel.

Figure 3:
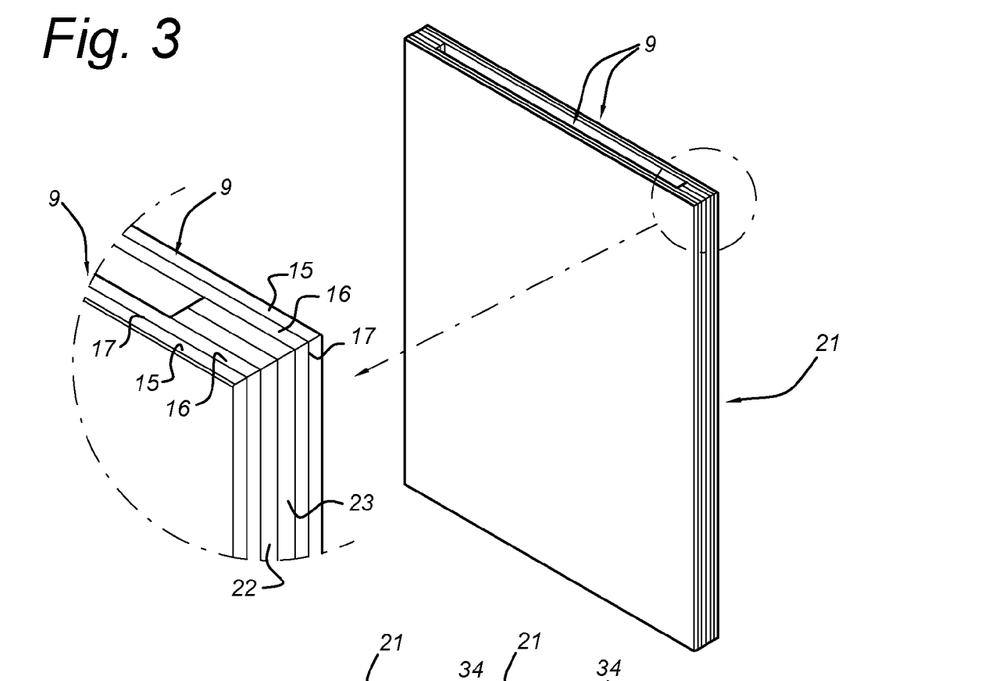

According to the invention, the double glass plates are advantageously arranged in pairs, with strips of glass joining the pairs along the long, vertical side of the plates, as further described below, and as depicted in FIG. 3.

The invention also pertains to double glass plates (pairs of glass plates with internal coating) as described above as well as to sets and arrays of double glass plates which can be used in photosynthetic reactors. The double glass plates preferentially have an essentially rectangular surface. The length (or height if positioned vertically) of the glass plates can be e.g. between 1 and 4 m, and preferably between 1.2 m and 2.4 m. The width of the glass plates can be e.g. between 0.5 and 2.5 m, preferably between 0.8 m and 2 m. Smaller surfaces may be suitable for pilot-type reactors. Larger surfaces may be feasible as well, although the weight and the handling of the glass plates may then require special measures. The thickness of the double glass plates can be as described above, i.e. between 20 and 60 mm, more preferably between 24 and 40 mm. The double glass plates have a layer of light-scattering particles in between, as described above.

Advantageously, two or more, in particular two, double glass plates are mounted together in parallel at a distance allowing an optimum reactor space between the two plates of from 10 to 200 mm, preferably from 20 to 150 mm or more preferably from 24 to 80 mm or even from 30 to 60 mm. The distance can be fixed by glass strips being positioned in between and along the length of the rectangular double glass plates. The strips thus essentially have the same length as the double glass plates, for example between 1 and 4 m. They may also have the same width, for example between 20 and 60 mm. Alternatively, they may have a width of e.g. 1-10 times, especially 2-4 times the thickness of the double glass plates, or alternatively 0.01 and 0.2 times, preferably 0.05-0.12 times the breadth (width) of the glass plates (for each strip). Thus a preferred strip width is e.g. between 2 and 20 cm, preferably between 2 and 15 cm or between 2 and 12 cm or in particular between 2.4 and 8 cm. Preferentially, the strips create a channel for algal reactor medium of the same size as the glass plate assembly, so the light exposure of the algal medium is the same in-between the glass assemblies as in the glass assembly.

The glass strips are preferably of the same glass type as the glass plates and are fixed to the glass plates using an appropriate sealant, such as a polymethacrylate sealant. The sets of two (or more) mounted double glass plates provide higher strength of the glass plates, and thus more convenient handling. The reactor vessel, or reactor unit, may thus advantageously contain between 2 and 12, more preferably between 4 and 10 of such fixed sets of double glass plates per m of reactor width, the sets being essentially mounted in parallel.

For facilitating the positioning and replacement of glass plates in the reactor vessel, sets of glass plates can advantageously be combined to an array of double glass plates or of sets of double glass plates described above. Thus, e.g. from 4 to 40, especially from 10 to 24 equidistant double glass plates, or from 2 to 20, especially from 5 to 12 equidistant sets of double glass plates, can be mounted together in a steel rack covered with a suitable, preferably flexible and/or compressible material, e.g. a thermoplastic polymer such as polypropylene or polyethylene, in such a way that the glass does not come into contact with the steel construction. The glass plate assemblies may be provided with suitable supports and guiding strips allowing the arrays to be mounted in the reactor vessel and combined as horizontal and/or vertical stacks. A useful stack of arrays of glass plates can e.g. be 3-6 racks stacked vertically and 2-5 racks horizontally.

The reactor dimensions are preferably such that a sufficient growth efficacy can be achieved through vertical circulation, while avoiding excessive internal pressures. It was found that reactor liquid heights of between 3 and 12 m, preferably between 5 and 10 m, most preferably between 7 and 9 m, provide an optimum result. Reactor widths (diameters), i.e. in the direction of the incoming light, are limited by the transmittance of light through normal ultra-clear float glass and typically not more than 2.5 m, preferably not more than 2.0 meter; suitable reactor widths are e.g. between 1 and 1.5 m. If desired, multiple reactor vessels can be stacked, so as to further upscale and economise the production performance. It is preferred that the reactor is made of steel, in particular coated steel or stainless steel.

In an advantageous embodiment, the reactor liquid can be provided with foam objects, which are moving with the circulating reactor liquid in order to clean the light emitting surfaces of the glass plates. Examples are sponge-type materials, for instance sponges made of melamine resin, in the size from e.g. 10 mm up to 30 mm, introduced at the bottom of the reactor in the up-flow part and collected at the top of the reactor. In operation of the reactor, the up-flow part and the down-flow part are regularly switched thus allowing both parts to be cleaned.

The means for vertically circulating reactor liquid are conveniently provided by the gas inlet means being arranged vertically below part of the spaces between the sets of glass plates. In particular, about half of the spaces between the glass plates is positioned above a part of the bottom of the reactor vessel which is provided with gas inlets, thus providing the upward flowing part of the reactor liquid, and the other half is positioned above a part of the bottom of the reactor vessel which is not provided with gas inlets, thus providing the downward flowing part of the reactor liquid. Advantageously, the gas inlets are provided in lines below half of the spaces between the double glass plates. The up-flow and down-flow compartments may be arranged alternatingly, or there may be a number of up-flow spaces followed by a number of down-flow spaces.

The light source comprises mirrors mounted on a sun tracking system reflecting sunlight to the flat sides of the glass plates. In this way, sunlight is reflected under a constant angle on the exposed part of the glass plates sticking in the gas lift loop channels of the reactor during the day.

In order to reduce the heating effect of the sunlight, the light source substantially only transmits light wavelengths between 400 and 700 nm. This means that the light intensity (in candela) of light having wavelengths below 400 nm and above 700 nm arriving at the glass plates is less than 50%, preferably less than 20% of the light intensity of light having a wavelength between 400 and 700 nm. For that purpose, the mirrors can advantageously be provided with a coating in such a way that the light wavelengths outside the 400 and 700 nm range are absorbed by the coating and thus not transmitted to the reactor. The skilled person will be able to select the appropriate UV absorbers and IR absorbers from commercially available alternatives.

The gas which is fed into the reactor vessel should comprise carbon dioxide needed for growth and photosynthesis of the algae. The gas source contains at least 0.5% (by vol.) of $CO_2$, preferably at least 5%, more preferably at least 10%, most preferably at least 30% (by vol.) of $CO_2$, the remainder being any gas, in particular nitrogen. The source of carbon dioxide can be a combustion gas originating from a fuel-combusting furnace, or a liquid or solid $CO_2$ source, or the like. Nutrients, such phosphorus, nitrogen, potassium ad micronutrients, may be added to the reactor as known in the art.

The invention also pertains to a process of producing algal products, such as algal oils, comprising culturing algae in a reactor vessel as described above and operated as an airlift loop reactor as known in the art per se. All photosynthetic microorganism, including green algae, red algae, cyanobacteria, etc., can be grown in the reactor vessel of the invention, using process parameters as known in the art. The algae can be harvested and isolated, or the algal products, especially fats for use as energy source "biodiesel" or as food source (long-chain polyunsaturated fatty acids), can be collected without the algae being isolated. Other commonly known algal product that can be produced and isolated by the process of the invention include algal proteins and carbohydrates, carotenoids and the like.

BRIEF DESCRIPTION OF THE DRAWINGS

Figure 1:
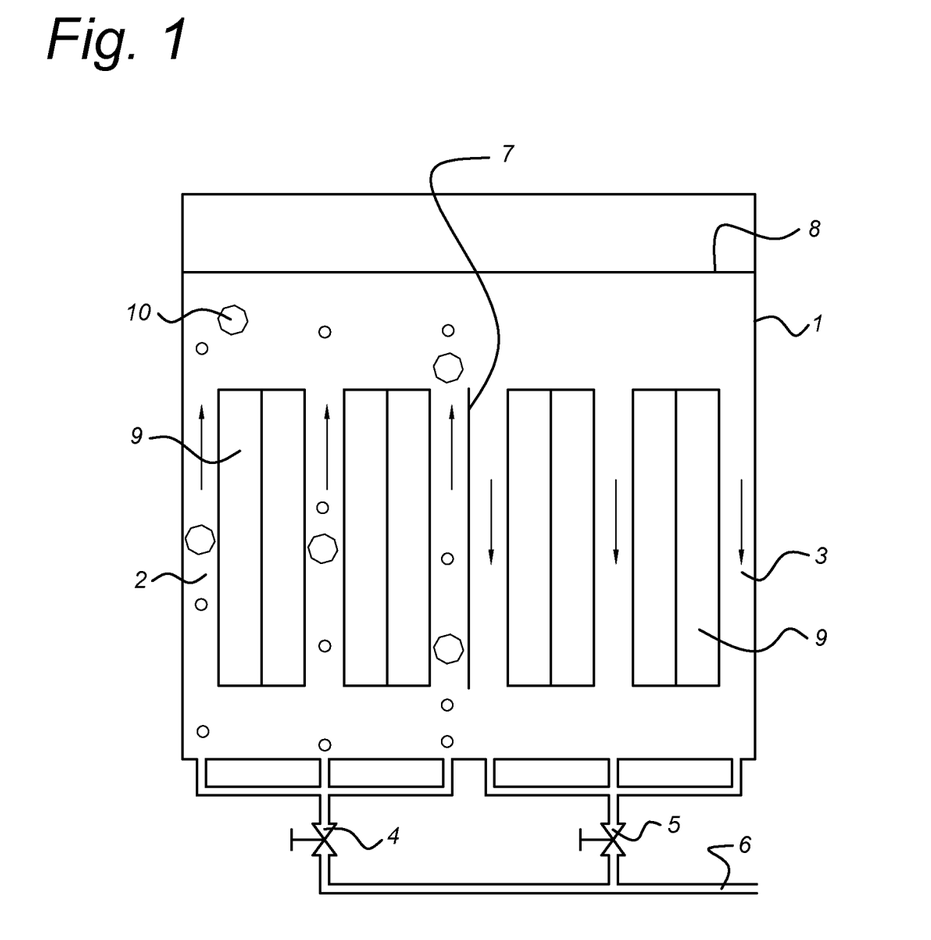

FIG. 1 schematically shows a section in the vertical plane of the reactor showing the principal parts thereof. A reactor vessel (1) is used for growing the algae. It has an up-flow channel (2) and a down-flow channel (3), which can alternate by switching the feeds (4) and (5) of the gas mixing flow (6). The up-flow and down-flow are separated by a vertical plate (7), the water level in the vessel is indicated with (8). To make this reactor suitable for algae growth, vertical glass plates (9) are installed in the up-flow and in the down-flow channels. Foam-like objects (10) move upward in the up-flow zone for cleaning the glass plates.

Figure 2:
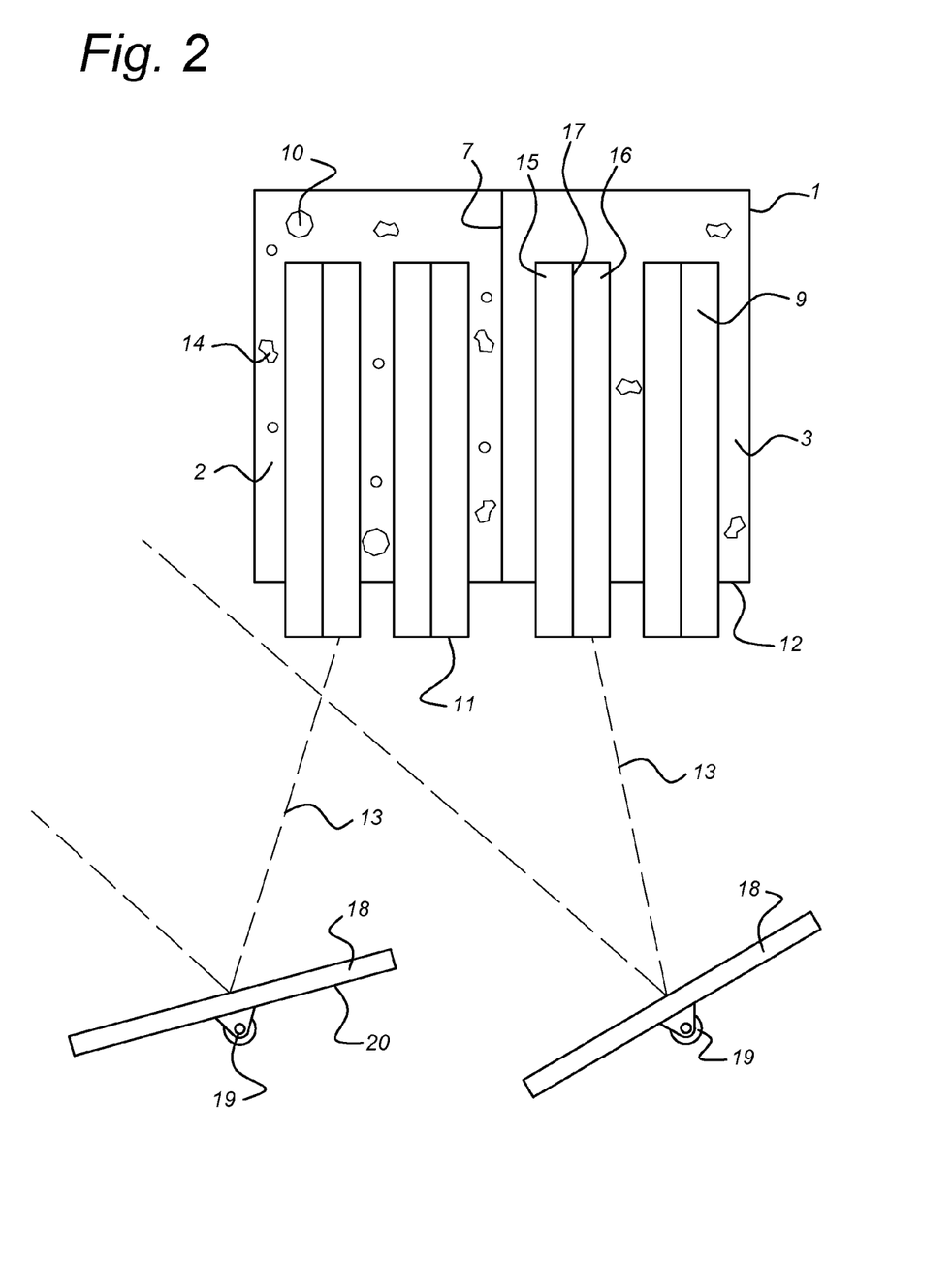

FIG. 2 shows a section in the horizontal plane of the reactor with the light mirror system. The vertical pairs of glass plates (9) in the up-flow zone (2) and down-flow zone (3) are shown. The front parts (11) of these plates are protruding from the reactor wall (12) into the light source (13). These glass plates (9) are used to transfer light into the reactor which is necessary for growth of the algae (14) inside the reactor (1). The glass plate consists of 2 layers (15) and (16) with a coating (17) in between, in which small metal parts are mixed that function as mirror facets to scatter the light in such a way that the light can enter the water.

A set of mirrors (18) is mounted on a sun-tracking system (19) to reflect the sunlight during the day under a constant angle on the exposed part of the glass plates sticking in the gas-lift-loop channels of the reactor. To reduce the heating effect of the sunlight, the mirrors (18) are provided with a coating (20) in such a way that only the wavelengths between 400 and 700 nm, necessary for algal growth, are reflected to the reactor.

FIG. 3 shows a set of double glass plates in more detail. The set of glass plates (21) is composed of two double glass plates (9). The set of glass plates contains 4 glass plates (15,16 twice) with layers (17) of scattering particles in between. Two glass strips (22,23) are positioned and sealed between the inner glass plates.

Figure 4:
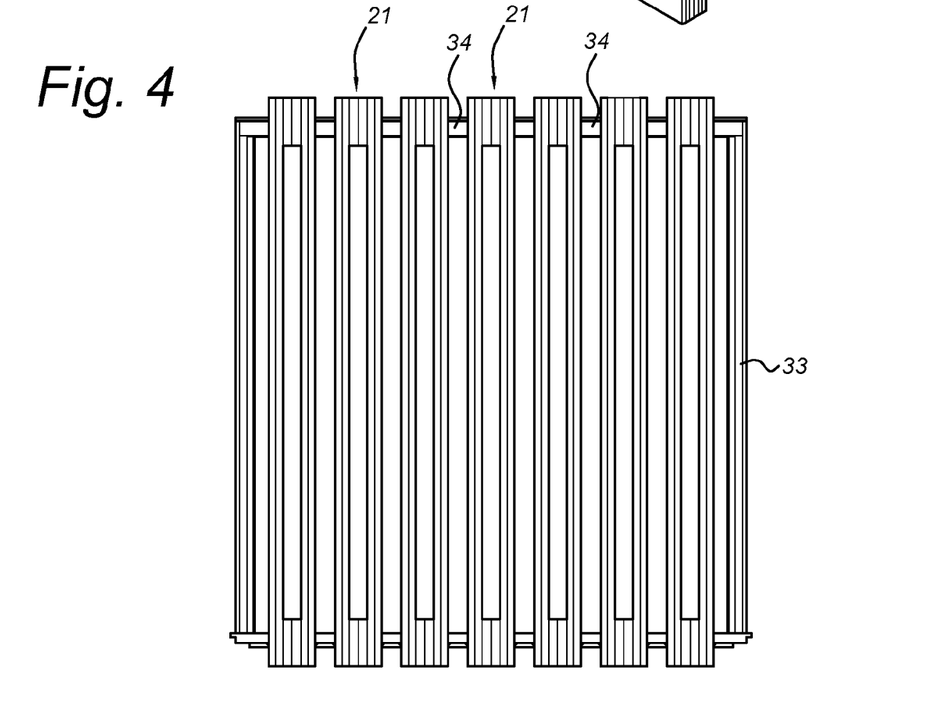

FIG. 4 shows a rack containing an array of double glass plates as a horizontal section (or top view). Sets of double glass plates (21) are mounted in a rack having side walls (33) and front and back walls comprising spacing strips (34) between the sets of glass plates.

Figure 5:
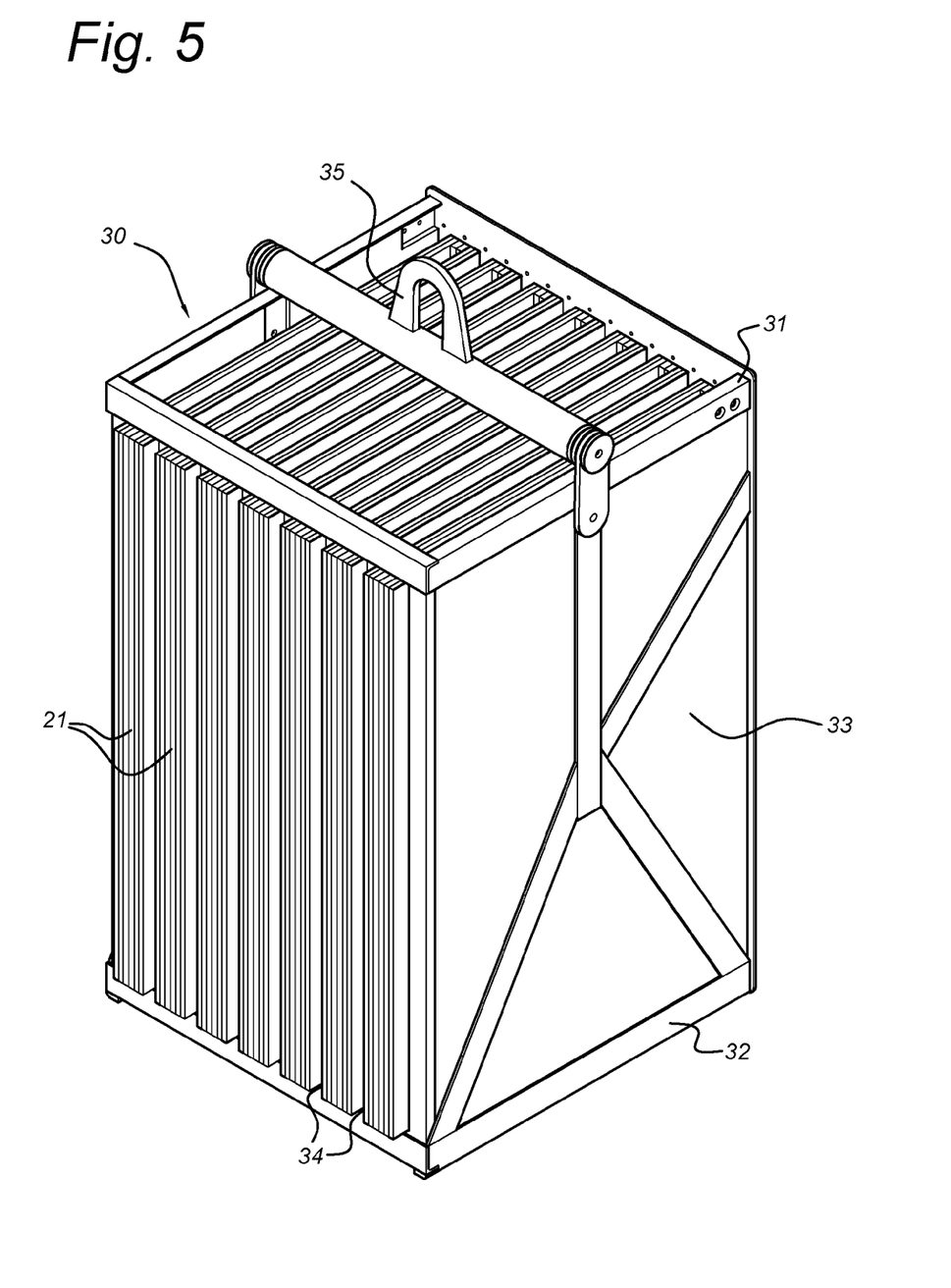

FIG. 5 shows the rack in perspective. The rack (30) comprises side walls (33) and strips (34) for spacing the glass plates as front and back walls. The rack has an upper part (31) and a lower part (32), for supporting the glass plates, and for allowing the racks to be stacked. A detachable device (35) for hoisting the rack into and out of the reactor vessel is mounted at the top of the rack.

Figure 6:
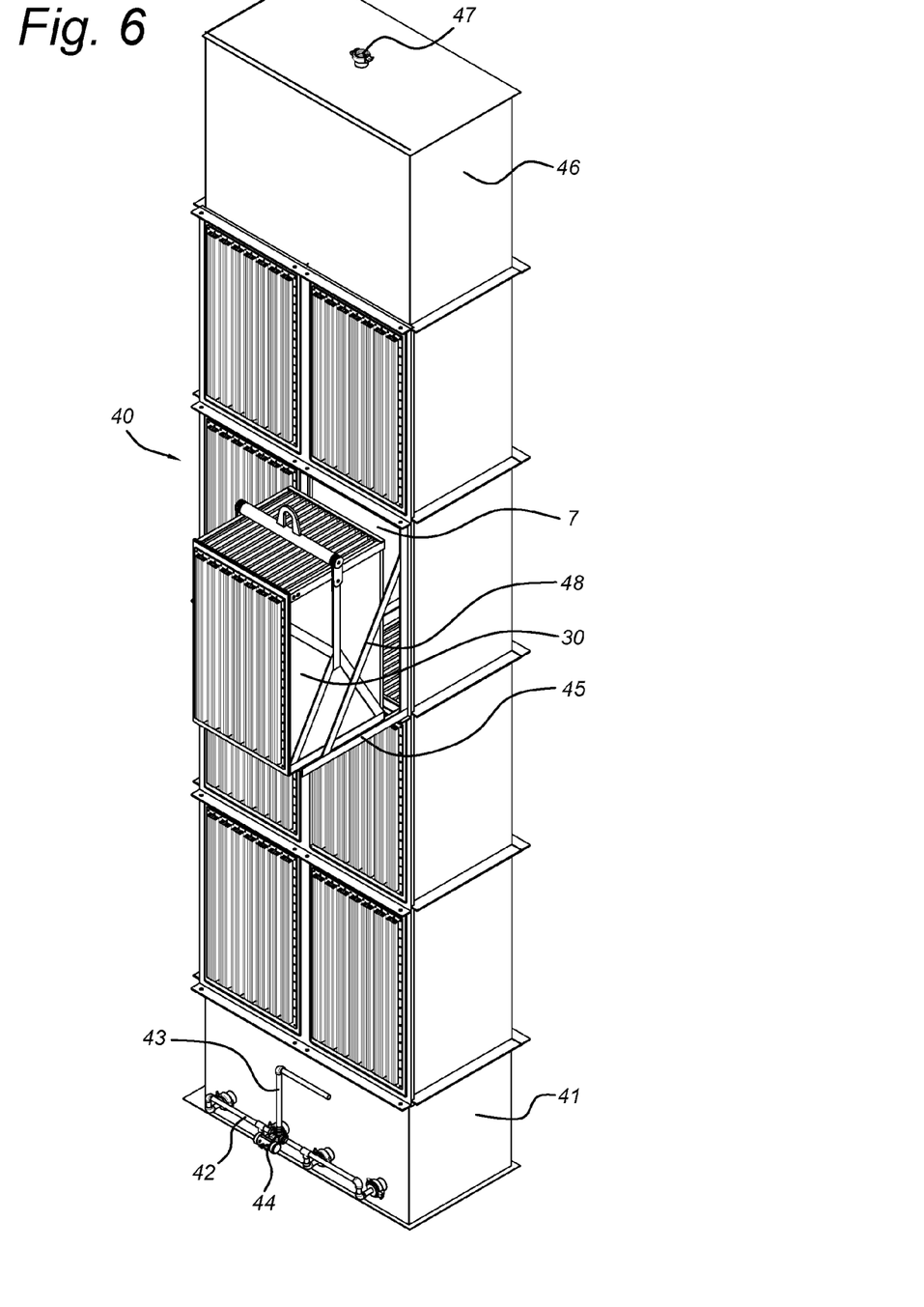

FIG. 6 shows a stacked reactor (40) containing eight racks (30) as depicted in FIG. 5. The stacked reactor has a bottom part (41) containing gas distributors driving the airlift loop (not shown) fed by gas pipes (42) connected to a gas supply (43), liquid/product lines and a liquid/product exit (not shown), and a top part (46) containing liquid inlets (not shown) and a gas exit (47). A three-way valve (44) between gas supply (43) and gas lines (42) allows to change the gas flow from one compartment to the other thus changing the riser part to downer part and vice versa. Guiding strips (45) supported by carrier strips (48) allow the racks (30) to be slid out of and into the stacked reactor assembly in case of e.g. maintenance or replacement.

The glass plates in the modules are stacked in such a way that they form continuous vertical channels from top to bottom of the stacked reactor. The separation baffle (7) between riser and downer parts runs over the height of the glass modules, so that the space over the glass modules and under is open. As a result, the reactor content (water and algae mixture) can circulate from riser to downer at the top, and from downer to riser in the bottom to create a closed loop.

While FIG. 6 shows two stacks of single racks, one serving as a riser and one as a downer part, more than two racks are equally feasible. For example, the reactor assembly may comprise three stacks, one as a riser, one as a downer, and the third one which can be switched off for maintenance or the like; in this case the valve (44) is a multi-way valve which ca be switched to either of the three or more stacks.

$CO_2$ can be injected in the air or gas mixture which drives the circulation loop and ensures the stripping of oxygen produced in the reactor. There is a level control in the reactor (not shown) and all water lost by harvesting of the algae and due to evaporation is pumped into the reactor at any point (total mixed system). Nutrients are fed into the reactor together with the make-up water.

The invention claimed is:

1. An airlift-loop reactor vessel, comprising:
   (a) one or more liquid inlets and one or more liquid outlets;
   (b) one or more gas inlets at the bottom, connected with a source of carbon dioxide, and one or more gas outlets at the top of the vessel;
   (c) vertically interspaced rectangular double glass plates which are at least partially submerged in the reactor liquid, the double glass plates having a light-scattering layer in between and having a flat vertical side being exposed to a light source,
   wherein pairs of the double glass plates are mounted in parallel at a distance of between 10 and 200 mm, the distance being provided by glass strips having essentially the same length as the rectangular double glass plates and being arranged along the long sides of the double glass plates; and
   wherein part of the spaces between the double glass plates is arranged vertically above the gas inlets thus providing for vertical circulation of reactor liquid between the double glass plates.

2. The reactor according to claim 1, wherein the light-scattering layer comprises non-uniformities or particles having a size in the range of 0.2-1.2 µm, acting as Mie scatterers.

3. The reactor according to claim 2, wherein the non-uniformities or particles have a size in the range of 0.4-0.8 µm.

4. The reactor according to claim 1, wherein the light-scattering layer comprises facetted particles having a size in the range of 5 µm to 500 µm, acting as geometric scatterers.

5. The reactor according to claim 1, wherein the light-scattering layer comprises a ceramic matrix, containing the light-scattering particles.

6. The reactor according to claim 5, wherein the ceramic matrix comprises silica.

7. The reactor according to claim 1, wherein the glass plates have a thickness of between 10 and 30 mm and the layer light-scattering layer has a thickness of between 10 and 1000 µm.

8. The reactor according to claim 1, wherein the pairs of double glass plates are vertically interspaced at a distance of between 20 and 120 mm.

9. The reactor according to claim 8, wherein the pairs of double glass plates are vertically interspaced at a distance of between 24 and 80 mm.

10. The reactor according to claim 1, wherein the vertically interspaced glass plates have a height of between 1 and 4 m.

11. The reactor according to claim 1, wherein the light source comprises mirrors mounted on a sun tracking system reflecting sunlight to the flat sides of the glass plates.

12. The reactor according to claim 11, wherein the mirrors comprise a coating to reflect only light wavelengths between 400 and 700 nm.

13. The reactor according to claim 1, wherein the reactor dimensions allow a reactor liquid height of between 5 and 10 m.

14. The reactor according to claim 1, wherein foam objects are moving with the circulating reactor liquid in order to clean the light emitting area of the glass plates.

15. A process of producing algal products, comprising:
   (a) providing a reactor comprising:
      (i) one or more liquid inlets and one or more liquid outlets;
      (ii) one or more gas inlets at the bottom, connected with a source of carbon dioxide, and one or more gas outlets at the top of the vessel;
      (iii) vertically interspaced rectangular double glass plates which are at least partially submerged in the reactor liquid, the double glass plates having a light-scattering layer in between and having a flat vertical side being exposed to a light source,
   wherein pairs of the double glass plates are mounted in parallel at a distance of between 10 and 200 mm, the distance being provided by glass strips having essentially the same length as the rectangular double glass plates and being arranged along the long sides of the double glass plates; and
   wherein part of the spaces between the double glass plates is arranged vertically above the gas inlets thus providing for vertical circulation of reactor liquid between the double glass plates
   (b) culturing algae in the reactor vessel, and optionally,
   (c) harvesting the algae and isolating the algal products.

16. The process according to claim 15, in which the algal products comprise algal oils.

17. The process according to claim 15, further comprising harvesting the algae and isolating the algal products.

* * * * *